(12) United States Patent
Thal et al.

(10) Patent No.: US 10,173,021 B2
(45) Date of Patent: Jan. 8, 2019

(54) TRACHEAL CANNULA AND SPEAKING-RESPIRATION SYSTEM FOR MECHANICAL RESPIRATION

(71) Applicant: Universitätsmedizin der Johannes Gutenberg-Universität Mainz, Mainz (DE)

(72) Inventors: Serge Thal, Walluf (DE); Philipp Tsafoulis, Wadern (DE)

(73) Assignee: UNIVERSITÄTSMEDIZIN DER JOHANNES GUTENBERG-UNIVERSITÄT MAINA, Mainz (DE)

(*) Notice: Subject to any disclaimer, the term of this patent is extended or adjusted under 35 U.S.C. 154(b) by 615 days.

(21) Appl. No.: 14/770,356

(22) PCT Filed: Mar. 10, 2014

(86) PCT No.: PCT/EP2014/054590
§ 371 (c)(1),
(2) Date: Aug. 25, 2015

(87) PCT Pub. No.: WO2014/135705
PCT Pub. Date: Sep. 12, 2014

(65) Prior Publication Data
US 2016/0001026 A1    Jan. 7, 2016

(30) Foreign Application Priority Data
Mar. 8, 2013  (DE) .................. 10 2013 004 115

(51) Int. Cl.
*A61M 16/04*    (2006.01)
*A61M 16/16*    (2006.01)
(Continued)

(52) U.S. Cl.
CPC ...... *A61M 16/042* (2014.02); *A61M 16/0003* (2014.02); *A61M 16/0069* (2014.02);
(Continued)

(58) Field of Classification Search
CPC ............ A61M 16/042; A61M 16/0003; A61M 16/0069; A61M 16/0434; A61M 16/20;
(Continued)

(56) References Cited

U.S. PATENT DOCUMENTS 4,280,492 A  *  7/1981  Latham ............. A61M 16/0468
                                                        128/207.15
4,459,984 A  *  7/1984  Liegner .................. A61F 2/203
                                                        128/207.15
4,612,664 A  *  9/1986  Walsh ................. F16K 31/0682
                                                        381/70

(Continued)

FOREIGN PATENT DOCUMENTS

GB         1 040 425 A       8/1966
WO       WO 86/02564 A1      5/1986
WO      WO 2005/112796 A2   12/2005

*Primary Examiner* — Joshua Lee
(74) *Attorney, Agent, or Firm* — Saliwanchik, Lloyd & Eisenschenk

(57) ABSTRACT

The present invention relates to a novel tracheal cannula (10), which allows patients to speak who receive artificial respiration with compressed-air. The tracheal cannula according to the invention makes this possible without the risk that saliva or stomach content is aspirated and without the occurrence of a loss of pressure during the respiration. This is achieved by an embodiment of the cannula having a separated speaking conduit (12) and respiration conduit (11). Furthermore, the invention relates to a speaking respiration system that can be connected to the tracheal cannula of the present invention, and that when used in a patient monitors (Continued)

Figure 1:
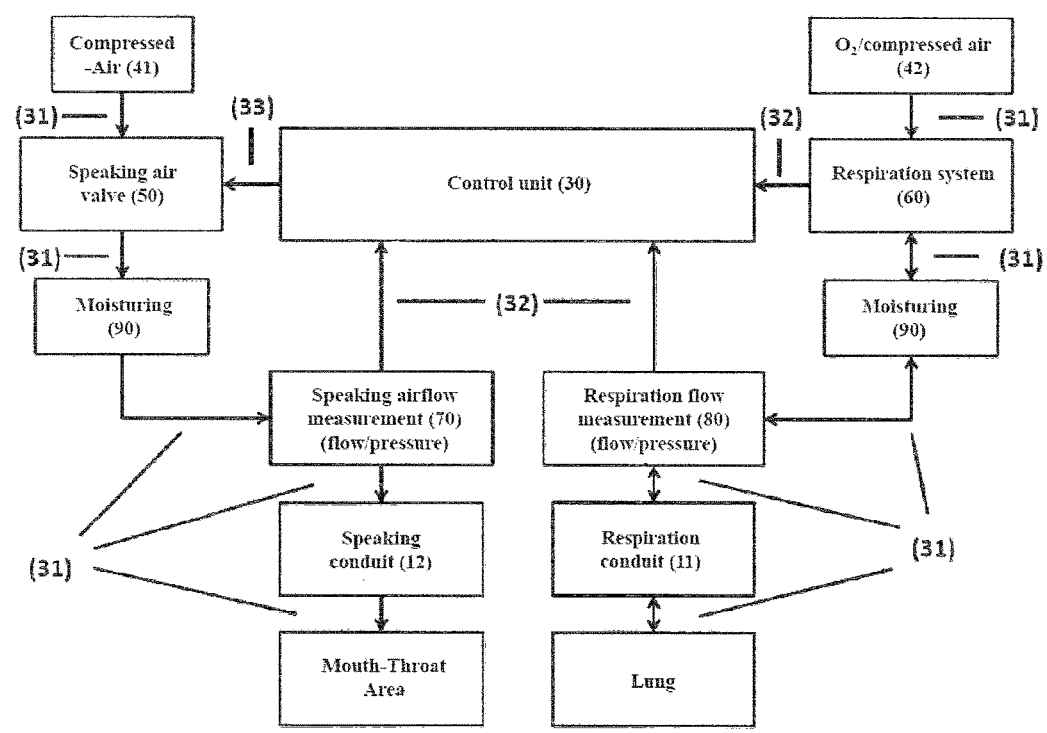

and controls the respiration of the patient, and simulates an artificial exhalation that enables the tracheostomized patient to speak.

7 Claims, 3 Drawing Sheets

(51) Int. Cl.
*A61M 16/20* (2006.01)
*A61M 16/00* (2006.01)

(52) U.S. Cl.
CPC .... *A61M 16/0434* (2013.01); *A61M 16/0463* (2013.01); *A61M 16/0465* (2013.01); *A61M 16/0468* (2013.01); *A61M 16/16* (2013.01); *A61M 16/20* (2013.01); *A61M 16/0479* (2014.02); *A61M 16/0486* (2014.02); *A61M 2016/003* (2013.01); *A61M 2016/0027* (2013.01); *A61M 2016/0036* (2013.01); *A61M 2205/3334* (2013.01)

(58) Field of Classification Search
CPC .......... A61M 16/0463; A61M 16/0465; A61M 16/0468; A61M 16/16; A61M 16/0479; A61M 16/0486; A61M 2016/003; A61M 2016/0036; A61M 2016/0027; A61M 2205/3334
See application file for complete search history.

(56) References Cited

U.S. PATENT DOCUMENTS

| | | | |
|---|---|---|---|
| 4,633,864 A * | 1/1987 | Walsh | A61F 2/20 128/207.15 |
| 4,637,389 A | 1/1987 | Heyden | |
| 4,773,412 A * | 9/1988 | Blom | A61F 2/203 128/207.14 |
| 5,515,844 A * | 5/1996 | Christopher | A61M 16/10 128/200.26 |
| 6,557,554 B1 * | 5/2003 | Sugiura | A61M 16/0096 128/204.18 |
| 8,770,193 B2 * | 7/2014 | Wondka | A61M 16/024 128/204.21 |
| 2007/0144526 A1 * | 6/2007 | Blom | A61M 16/0468 128/207.16 |
| 2008/0060646 A1 * | 3/2008 | Isaza | A61M 16/0468 128/204.21 |
| 2009/0095302 A1 * | 4/2009 | Blom | A61M 16/0465 128/207.16 |
| 2009/0156953 A1 * | 6/2009 | Wondka | A61M 16/0465 600/538 |
| 2009/0235936 A1 * | 9/2009 | Blom | A61M 16/0465 128/207.16 |
| 2013/0340748 A1 * | 12/2013 | Alqudah | A61M 16/0468 128/200.26 |
| 2014/0238398 A1 * | 8/2014 | Christopher | A61M 16/0816 128/204.22 |

\* cited by examiner

TRACHEAL CANNULA AND SPEAKING-RESPIRATION SYSTEM FOR MECHANICAL RESPIRATION

CROSS REFERENCE TO RELATED APPLICATIONS

This application is a National Stage Application of International Application Number PCT/EP2014/054590, filed Mar. 10, 2014; which claims priority to German Application No. 10 2013 004 115.5, filed Mar. 8, 2013; both of which are incorporated herein by reference in their entirety.

The present invention relates to a novel tracheal cannula, which allows patients to speak who receive artificial respiration with compressed-air. The tracheal cannula according to the invention makes this possible without the risk that saliva or stomach content is aspirated and without the occurrence of a loss of pressure during the respiration. This is achieved by an embodiment of the cannula having a separated speaking conduit and respiration conduit. Furthermore, the invention relates to a speaking respiration system that can be connected to the tracheal cannula of the present invention, and that when used in a patient monitors and controls the respiration of the patient, and simulates an artificial exhalation that enables the tracheostomized patient to speak.

DESCRIPTION

Wake patients suffering from a lung disorder or from a general exhaustion often have to receive mechanical respiration for a prolonged period (>5 days). In these patients, a tracheotomy is often performed. A tracheotomy is a cut in the patient's trachea where an access to the trachea is placed through the soft tissue of the neck. Into this access a specially designed cannula (tracheal cannula) is inserted. The tracheal cannula keeps the access open and facilitates the artificial respiration by an inflatable "balloon" or "cuff" which seals the space between the trachea and the cannula. A typical tracheal cannula comprises an elongated proximal part provided with a cuff or balloon that is inserted concentrically into the trachea. Above the proximal part a curved part is arranged which connects the cannula via the access with the environment and that provides a link to a respiration system. The balloon or cuff seals the space between the trachea and the tracheal cannula and thus allows to establish a sufficient pressure in the lungs when breathing air is supplied by the respiration system, and prevents throat fluids to enter the lungs.

Patients receiving artificial respiration using compressed air with the state of the art systems can only poorly, or not all, talk. This prohibits verbal communication with the patient, and leads to isolation, in particular if the patient receives artificial respiration for a long time. Further, speaking as a breathing exercise does not take place and the associated physiological functions are omitted. Currently speaking becomes only possible when the patients is able to breath without pressure support, after the patient's complete withdrawal from mechanical respiration, and by using a so-called speaking-cannula or "Unblocking" of a conventional tracheal cannula and attachment of a speaking valve.

The patent publication WO 95/14499 discloses a tracheal cannula for artificial respiration of tracheostomized patients that has a cuff that surrounds and seals the proximal part of the tube capable of being concentrically inserted into the trachea, and a bent area arranged above said cuff, as well as an inner tube that may be concentrically inserted into the tube through its distal end. A breathing-out opening is provided in the tube above the trachea-sealing cuff as well as in the continuation of the longitudinal axis of the bent part that may be inserted into the trachea. In its area located below the breathing-out opening, the inner tube has a recess at least partially covered by an elastic membrane that acts as a valve.

During the inhalation phase, a given volume of air is forced by the respirator through the inner cannula introduced from the distal end into the trachea, through the proximal region of the tracheal cannula and the trachea into the lungs. Thereby the membrane disposed at the inner cannula should expand to the outside in the region of expiration opening of the tracheal cannula and thereby comes to rest at the inner surface along the peripheral edge of the expiration opening of the cannula. Thereby, the expiration opening is sealed and it is prevented that the introduced volume of air escapes directly via the upper respiratory tract instead flowing into the lungs. During the expiratory phase, this membrane contracts and opens an access to the expiration opening for the exhaled air. Via the pulmonary pressure caused by the pumped-in ventilation air in the lungs the exhaled air then flows into the throat and allows a vibration of the vocal cords. However, the cannula described is disadvantageous because the speaking time is exclusively dependent on the ventilation air flowing back from the lungs of the patient. However, weaker patients can only insufficiently modulate this return flow. Furthermore, due to the expiration opening of the tracheal cannula, the risk of aspirating or swallowing saliva or stomach contents is not excluded. Also the pressure in the lung at the end of the exhalation phase decreases to ambient pressure probably resulting in an alveolar collapse.

The patent application DE 10 2005 056 999 describes a tracheal cannula which consists of two tubes that connect the trachea of the patient with the environment. Through these tubes, breathing air is directed during both the inhalation phase as well as the exhalation phase. According to the disclosure the tubes on the outside end in a liquid separator, where saliva and mucus is removed from the breathing air. Although the disclosed cannula separates saliva, it can only be used in patients who can breathe without mechanical assistance, however suffer from a malfunction of the airways or larynx and therefore received a tracheostomy.

Thus, the prior art does not offer a satisfactory solution that permits patients to speak, for example, exhausted patients with pulmonary dysfunction who underwent a tracheotomy, and who have to be supplied with breathing air using compressed-air respiration for a long time and thus prevents isolation of the patient.

In a first aspect, the above-described problem is solved by a tracheal cannula (10) for active respiration (pressure assisted) of a patient, comprising a respiration conduit (11) and a speaking conduit (12), characterized in that the respiration conduit (11) and the speaking conduit (12) can be supplied with air independent of each other. Preferably, the tracheal cannula of the present invention is bent; in particular, it may be flexible in order to be easily inserted into the trachea of a patient. The tracheal cannula of the present invention is in a preferred embodiment formed in such a way that it can be used for active (pressure assisted) respiration of a patient.

The terms "air", "compressed air", "breathing air" or "respiration air" shall be understood in context of the herein described invention as an air composition that is suitable for the respiration of mammals, especially for human patients. Therefore, air in the context of the present invention shall be understood to refer in particular to the natural atmospheric air composition, or compositions that are very similar thereto. The atmospheric air is mainly composed of the gases oxygen (~21%) and nitrogen (~78%). In addition, there are carbon dioxide and argon, and other gases in traces.

For the respiration of patients with lung dysfunction and impaired uptake of oxygen an increase in the oxygen content of the breathing air may become necessary. The oxygen proportion for the respiration and speaking conduits is therefore adapted between 21-100% for each individual patient and controlled with measurement instrumentation. Such mixing and measuring systems are sufficiently described in the prior art. Therefore, the above terms "air", "compressed air", "breathing air" or "respiration air" refer also to air mixtures in which the $O_2$ content is increased.

In a preferred embodiment of the invention both the speaking conduit and the respiration conduit are integrated in one tracheal cannula. Alternatively the invention can be designed as an outer cannula comprising two inner cannulas, wherein the outer cannula is inserted into the trachea of a patient. Subsequently the two inner cannulas (souls) can be inserted into the outer cannula, wherein one inner cannula represents the respiration conduit and ensures the respiration of the lungs, whereas a second inner cannula as the speaking conduit ventilates only the mouth and throat area.

The term "active respiration" refers to an artificial respiration of the lung volume of a patient assisted by compressed air. This is used for patients who are too weak to inhale sufficient air by themselves using their thoracic diaphragm. These patients are therefore connected to a compressed air system that blows sufficient respiration air through the tracheal cannula into the lungs. Such systems are sufficiently described in the state of the art.

The cannula according to the present invention solves the posed problem because when it is inserted into a patient the separated respiration- and speaking conduits provide independently (i) the lung space with breathing air and (ii) ventilation of the mouth and throat area via the speaking conduit so that the patient is able to speak normally. By designing the tracheal cannula as two separate conduits, the risk of swallowing or accidently aspirating saliva or stomach contents is reduced. Also the patient is permitted to speak independently of the exhaled respiration air due to the separate control of the supply of "speaking air".

Therefore, the tracheal cannula according to the invention is in a preferred embodiment designed such that the respiration conduit (11) and the speaking conduit (12) form separate self-contained volumes. In this way it is prevented that air between the respiration conduit/lung and the speaking conduit/mouth-throat area is exchanged.

The tracheal cannula may be further characterized in that the respiration channel (11) has a connector for a respiration air system (13), and the speaking conduit (12) has a connector for a speaking air system (14). The connectors are disposed at the distal end of the cannula. The distal end of the cannula is located outside of the body of the patient when the cannula is used. The proximal end of the tracheal cannula is regarded as the end that has been inserted into the trachea of the patient.

The tracheal cannula of the present invention in a preferred embodiment is equipped with a sealing ring (20). The sealing ring (20) may also be referred to as "cuff" or "balloon" and is intended to fixate the cannula in the trachea and to seal-off the lung volume from the mouth and throat area. In order to establish the pressure necessary for the artificial respiration, the trachea must be sealed-off with the balloon (cuff) (20) located below the larynx. This seal ensures that the air contained in the lungs can escape exclusively through the tracheal cannula, in fact through the respiration conduit when an appropriate valve is opened in the respiration air system.

Preferred is further a tracheal cannula wherein the speaking conduit (12) comprises a speaking air outlet (16) granting the ventilation of the mouth and throat area, and wherein the speaking air outlet (16) is arranged such that it is disposed in the cannula on the outer wall of the speaking conduit, above the cuff (20) sealing the trachea, approximately in the extension of the longitudinal axis of the bent portion of the cannula that can be inserted into the trachea. In addition, the respiration conduit (11) comprises a respiration air outlet (15) granting the respiration of the lungs. The respiration air outlet (15) is disposed below the sealing cuff (20).

Therefore, it is preferable that the sealing ring (20) is disposed between the air outlets (15) and (16), that is, below the speaking air outlet (16), allowing for a separate ventilation/respiration of the mouth-throat area and the lung during the respiration of a patient.

Thus, during active respiration using a tracheal cannula according to the invention the airways located above the sealing cuff (20) are completely bypassed, in particular the area of the mouth and throat. The expiratory volume can thus no longer flow through the larynx. For generating sounds during speaking the vocal cords must be brought into a swinging movement (Bernoulli—vibrations) to permit a phonation. This function is therefore realized by a separate speaking air supply via the speaking conduit of the tracheal cannula according to the invention. Sufficient air can be blown through the speaking conduit in order to bring the vocal cords into vibration and to allow the patient to speak. This is preferably performed during the exhalation phase of respiration.

In one embodiment, the inventive tracheal cannula comprises an air impermeable inner wall (18) that cuts off a portion of the tracheal cannula from the main volume of the cannula to form a separate speaking conduit. In a particularly preferred embodiment, the inner wall (18) is collapsible, so that it collapses the speaking conduit (12) during the inhalation phase when compressed air is blown through the respiration conduit into the lungs. During the exhalation phase speaking air is blown through the speaking conduit, so that the speaking conduit (12) expands again (FIGS. 2B and C).

In an alternative embodiment of the tracheal cannula comprising a collapsible wall (18), as described before, the collapsible inner wall (18) is composed of a flexible material. Additionally, when the collapsible inner wall (18) collapses the volume of the speaking conduit (12) is reduced, therefore at the same time the speaking conduit (12) as such is collapsed. The collapsible wall (18) is fixated at the inner wall of the tracheal cannula (10). The fixation must ensure that the airflow in the volume that is cut-off and forms the speaking conduit (12) and the remaining volume of the tracheal cannula forming the respiration conduit (11) is separated, thus that no air can bypass the inner wall (18). Therefore in this embodiment the tracheal cannula of the invention essentially comprises a collapsible speaking conduit (12), having a volume that is reduced when compressed-air is blown into the respiration conduit (11) into the lungs, and that increases when compressed-air is blown into the mouth and throat area via the speaking conduit (12).

In an alternative embodiment of the invention, the tracheal cannula is designed as a double-walled cannula—thus as a double tube. In this embodiment the tracheal cannula also comprises two volumes that are separated from each other. One volume is disposed between the outer wall of the tracheal cannula (10) and the wall of the inner tube located in the inside of the tracheal cannula. This volume represents the speaking conduit (12). The volume of the inner tube represents the volume of the respiration conduit (11). As described above both volumes are separated from each other hermetically.

The tracheal cannula according to the invention, wherein the respiration conduit (11) and the speaking conduit (12) provide a connection of the patient's trachea with the environment when the tracheal cannula is inserted into a patient.

In a second aspect, the object of the invention is solved by a respiration system for active respiration of a patient, which is designed that it can be connected to a tracheal cannula (10) as described above.

In a preferred embodiment, the respiration system further comprises:
 a. a control unit (30) which creates a exhalation profile on the basis of the exhalation pattern of a patient,
 b. a speaking air valve (50) which connects a compressed air source with the speaking conduit (12), and that is controlled by the control unit (30),
 c. and a respiration air system (60) that connects a compressed air source with the respiration conduit (11).

Here the control unit (30) allows the simulation of an artificial exhalation on basis of the exhalation profile via control of the speaking air valve (50); and the artificial exhalation allows for a speaking that is independent of the artificial respiration. A preferred construction of a respiration system of the invention is shown schematically in FIG. 1. This is a prototype configuration of a so-called "T-Vent" system.

The respiration system of the present invention (T-Vent System) is a combination of an improved tracheal cannula as described above and a computer-controlled speaking system that monitors the breathing cycle of the patient and allows speaking during the exhalation phase by an adapted additional air flow in the direction of vocal cords. By means of a measuring unit the expiration of the patient is measured (flow and pressure measurement), rated (computer-aided analysis) and an exhalation profile is created (FIG. 1). The patient receives via a separate lumen of the tracheal cannula (FIGS. 2, 3) the calculated additional, controlled air flow (flow and pressure measurement) that imitates the exhalation through the mouth and thus lets the vocal cords vibrate (Bernoulli vibrations) and makes a phonation possible. The respiration of the patient is not changed or influenced by the T-Vent system.

Therefore, the respiration system preferably comprises further a speaking air measurement unit (70) measuring the speaking air flow and pressure, and transmitting the data to the control unit (30); and a respiration air measuring unit (80), measuring the respiration air flow and pressure, and transmitting the data to the control unit (30), wherein the respiration air measuring unit (80) can measure flow and pressure during both inhalation and exhalation.

It is advantageous that both the speaking air and the respiration air can be humidified before being blown into the tracheal cannula. Therefore, the respiration system may further include at least one air dampening system (90) that humidifies the respiration air and/or speaking air.

The respiration system further comprises at least one compressed air source (40), providing the respiration air system (60) and/or the speaking air valve (50) with compressed air, or breathing air respectively. Preferred is a respiration system wherein the mouth and throat area of a patient is supplied with air via the speaking conduit (12), and the patient's lungs is supplied with air via the respiration conduit (11), wherein the air supply is preferably carried out separately from each other.

Alternatively it is preferred that when the respiration system is used at a patient, the mouth and throat area of the patient is supplied with air via the speaking conduit (12), and the patient's lungs are supplied with air via the respiration conduit (11), wherein the air supply of the speaking conduit and the respiration conduit is preferably carried out separately from each other, therefore by using two separate air sources.

Particularly preferred is an above-described respiration system, comprising a tracheal cannula as described above.

A respiration system of the invention has a number of advantages compared to the known prior art systems. For patients the system allows to overcome isolation, for example, in that it allows verbal communication with relatives and hospital staff. For the treating doctors/nurses: direct communication with the treated patient, and thereby better monitoring of neurological status, pain, etc., faster withdrawal from mechanical respiration because of an increased motivation and bio-feedback, avoidance of PEEP loss. The system provides for the direct de-cannulation of the patient, bypassing the so-called "artificial nose". Due to the natural ventilation of the paranasal sinuses the risk of infections of the patient is reduced and unobstructed respiratory passages are ensured/controlled.

The present invention is described in detail below with reference to individual embodiments and figures. The examples shown here shall not to be understood as a limitation of the general inventive principle.

The figures show:

FIG. 1: shows a schematic representation of a respiration system of the present invention. Arrows indicate the flow direction of air (31), data (32) or of control commands (33).

Figure 2:
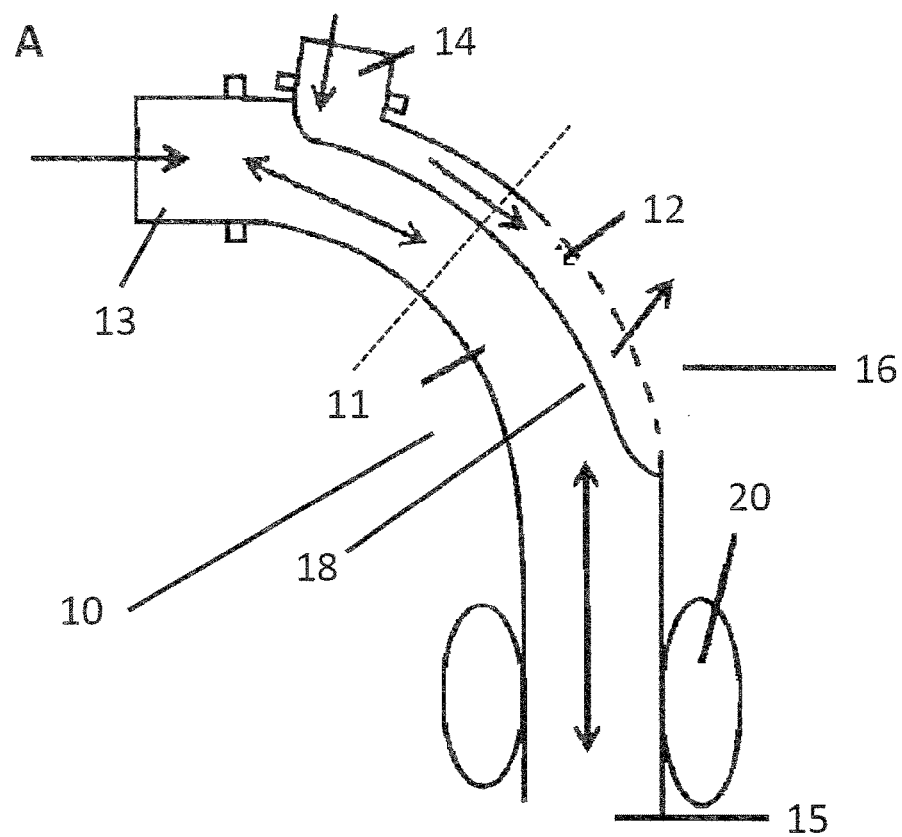
Figure 2:
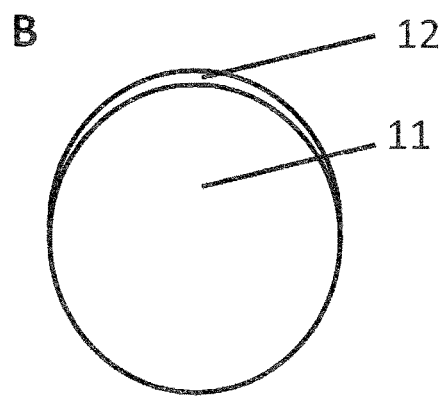
Figure 2:
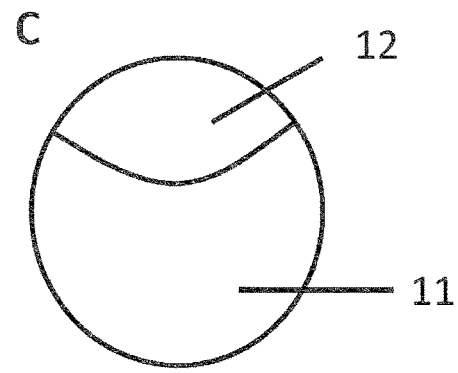

FIG. 2: shows a preferred tracheal cannula of the invention. The illustrated embodiment is characterized by a collapsible speaking conduit A: arrows indicate the respective direction of the flow of the speaking- or respiration air. The dashed line marks the cross-section of the tracheal cannula shown in B and C. B: Shows the cross-section of the tracheal cannula during the inhalation phase (speaking conduit collapses), C: Shows the cross-section of the tracheal cannula during exhalation phase (speaking conduit ventilated).

Figure 3:
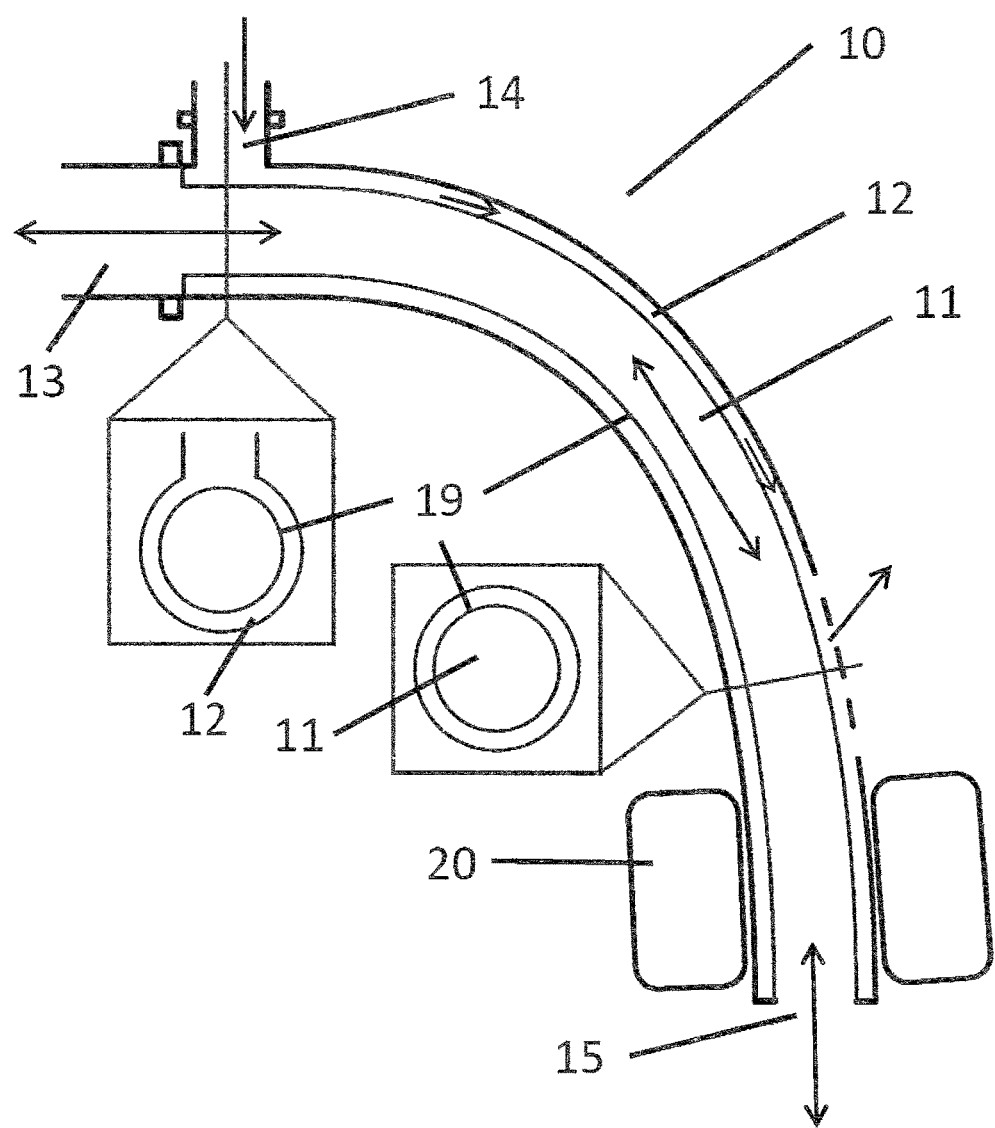

FIG. 3: shows a second preferred tracheal cannula of the present invention. The shown embodiment includes a double-tube where the external volume represents the speaking conduit and the internal volume channels the respiration air to the lungs. Arrows indicate the respective flow direction of the speaking-, and respiration air. Boxes show cross-sections of the cannula at the respective positions.

The following reference numerals are used in the drawings
10 Tracheal cannula
11 Respiration conduit
12 Speaking conduit
13 Connector for a respiration air system
14 Connector for a speaking air system (T-Vent)
15 Outlet of the respiration conduit towards the lung
16 Air outlet of the speaking conduit in the direction of the mouth and throat area
18 Inner wall
19 Inner tube wall
20 Seal ring, or "cuff", "balloon"
30 Speaking air control unit
31 Air flow 32 Measurement data
33 Control command
40 Compressed-air source
41 Compressed-air source (turbine) for speaking-air
42 Compressed-air source (turbine) for respiration-air ($N_2$/$O_2$)
50 Speaking air valve
60 Respiration air system
70 Speaking air measurement unit
80 Respiration air measurement unit
90 Air dampening system

EXAMPLES

Example 1

FIG. 1 shows a preferred speaking air system according to the present invention. Central is the control system (30) which creates an exhalation profile of a patient connected to the system on the basis of measured data (92) retrieved from a respiration flow measurement unit (80), and from the respiration air system (60), which controls the mechanical inhalation and -exhalation during a respiration with compressed air. Based on the exhalation profile the system (30) controls a speaking air valve (50). By opening the valve speaking air can be channeled from a compressed air source (41) into the system. The control unit (30) simulates an artificial exhalation of the patient by opening the valve. The speaking air is therefore channeled into the system, into the speaking conduit of the tracheal cannula of the invention and thus into the mouth and throat area during an exhalation phase, in order to allow the patient a phonation. The stream (pressure and flow) of the speaking air is at the same time monitored by a measuring unit (70), which forwards the obtained data to the control system (30). The system can also comprise a unit (90) for moistening of the speaking- and respiration air. FIG. 1 illustrates the separated flow of respiration- and speaking air (left/right).

Example 2

One embodiment of the tracheal cannula described in this application is shown in FIG. 2. The tracheal cannula (10) comprises two conduits (11) and (12) which are separated by an air-impermeable inner wall (18). Thus, both conduits have separate air inlets and outlets (13)/(14) and (15)/(16). In FIG. 2 A, the flow-direction of the air to be blown in is indicated by arrows. The inner wall (18) is collapsible in this embodiment. In the inhalation phase respiration air is pumped through the respiration conduit (11) into the lungs of the patient. Since no speaking occurs during the inhalation phase, the speaking conduit (12) remains unventilated. The collapsible inner wall (18) therefore attaches to the outer wall of the tracheal cannula due to the pressure of the blown-in respiration air and increases the volume of the respiration conduit.

During the exhalation phase speaking air is blown with an externally connected speaking air system through the speaking conduit into the mouth and throat area of a patient, in order to allow the patient to speak. Therefore the speaking conduit expands during the exhalation phase due to the pressure of the blown-in speaking air.

Example 3

FIG. 3 shows a second embodiment of the tracheal cannula of the present invention. Here, the tracheal cannula (10) is formed as a double tube (see the cross-sections shown in FIG. 3). Through the outer volume (12), the speaking conduit, speaking air can also be blown into the mouth and throat area. The inner tube wall (19) does not collapse here. Via the inner tube volume (11) the respiration air is channeled into the lungs of a patient.

The invention claimed is:

1. A respiration system, adapted to be connected to a tracheal cannula for active respiration of a patient, comprising:
a control unit that creates an exhalation profile on the basis of an exhalation pattern of a patient,
a speaking air valve, adapted to connect a compressed air source with a speaking conduit in the tracheal cannula, that is controlled by the control unit; and
a respiration air system adapted to connect a compressed air source with a respiration conduit in the tracheal cannula, wherein the control unit simulates an artificial exhalation on the basis of the exhalation profile via control of the speaking air valve, and thereby allows for speaking that is independent of the artificial exhalation, and wherein the respiration conduit and the speaking conduit are supplied with air independent of each other.

2. The respiration system according to claim 1, further comprising at least one air dampening system that humidifies the air supplied in the respiration conduit and/or the speaking conduit.

3. The respiration system according to claim 1, further comprising at least one compressed air source, providing the respiration air system and/or the speaking air valve with compressed air.

4. The respiration system according to claim 1, wherein a mouth and throat area of a patient is supplied with air via the speaking conduit, and the patient's lungs are supplied with air via the respiration conduit, wherein an air supply is preferably provided separately from each other.

5. A respiration system for providing active respiration, according to claim 1, which comprises a tracheal cannula for active respiration (pressure assisted) of a patient.

6. A respiration system, adapted to be attached to a tracheal cannula for active respiration of a patient, comprising:
a speaking air measurement unit, adapted to be operably connected to a speaking conduit in the tracheal cannula, for measuring a speaking air flow and pressure, and transmitting the measured speaking air flow and pressure data to a control unit; and
a respiration air measuring unit, adapted to be operably connected to a respiration conduit in the tracheal cannula, for measuring a respiration air flow and pressure and transmitting the measured respiration air flow and pressure data to the control unit, wherein the respiration air measuring unit measures flow and pressure during both inhalation and exhalation, and wherein the respiration conduit and the speaking conduit are supplied with air independent of each other.

7. A respiration system for providing active respiration, according to claim 6, which comprises a tracheal cannula for active respiration (pressure assisted) of a patient.

* * * * *